(12) United States Patent
Sabeti

(10) Patent No.: US 8,998,867 B2
(45) Date of Patent: Apr. 7, 2015

(54) MEDICAL DEVICE

(75) Inventor: Saied Sabeti, Hocking (AU)

(73) Assignee: Saied Sabeti, Hocking (AU)

( * ) Notice: Subject to any disclaimer, the term of this patent is extended or adjusted under 35 U.S.C. 154(b) by 0 days.

(21) Appl. No.: 13/564,598

(22) Filed: Aug. 1, 2012

(65) Prior Publication Data

US 2013/0030397 A1   Jan. 31, 2013

Related U.S. Application Data

(63) Continuation of application No. PCT/AU2011/000094, filed on Feb. 1, 2011.

(30) Foreign Application Priority Data

Feb. 1, 2010   (AU) .................................. 2010900379

(51) Int. Cl.
*A61F 5/44* (2006.01)
*A61F 5/445* (2006.01)
*A61F 5/441* (2006.01)
*A61F 5/449* (2006.01)

(52) U.S. Cl.
CPC ......... *A61F 5/445* (2013.01); *A61F 2005/4455* (2013.01); *A61F 2005/4415* (2013.01); *A61F 5/4405* (2013.01); *A61F 5/441* (2013.01); *A61F 2005/4495* (2013.01)

(58) Field of Classification Search
USPC ........................................................ 604/335
See application file for complete search history.

(56) References Cited

U.S. PATENT DOCUMENTS

| 2,542,233 A * | 2/1951 | Carroll ........................... 604/337 |
| 3,565,073 A | 2/1971 | Giesy |
| 3,893,469 A * | 7/1975 | Baker ............................. 137/584 |
| 4,147,184 A * | 4/1979 | Jess ........................... 137/625.47 |
| 4,205,678 A | 6/1980 | Adair |
| 4,241,735 A * | 12/1980 | Chernov ........................ 606/192 |

(Continued)

FOREIGN PATENT DOCUMENTS

| CN | 2293305 Y | 10/1998 |
| CN | 101056599 A | 10/2007 |

(Continued)

OTHER PUBLICATIONS

International Preliminary Report on Patentability for International Application No. PCT/AU2011/000094, International Preliminary Examining Authority/Australia, mailed May 18, 2012, 17 pages.

(Continued)

*Primary Examiner* — Tatyana Zalukaeva
*Assistant Examiner* — Guy K Townsend
(74) *Attorney, Agent, or Firm* — Marger Johnson & McCollom PC

(57) ABSTRACT

An ostomy device (1) has an implant (10) arranged, in use, to be located inside the body of person near the site of a stoma (S). A discharge device (20) is arranged, in use, to provide means for intestinal waste to exit to the exterior of the body of the person. In addition, there is means, in use, to be operatively associated with the implant (10) and removably locate the discharge device (20) at the site of the stoma (S). The discharge device (20) is retained at the site of the stoma (S) by magnetic attraction between the implant (10) and the discharge device (20).

28 Claims, 14 Drawing Sheets

(56) References Cited

U.S. PATENT DOCUMENTS

| | | | |
|---|---|---|---|
| 4,338,937 A | | 7/1982 | Lerman |
| 4,344,434 A | | 8/1982 | Robertson |
| 4,351,322 A | * | 9/1982 | Prager .............................. 600/32 |
| 4,381,765 A | * | 5/1983 | Burton ............................. 600/32 |
| 4,634,421 A | * | 1/1987 | Hegemann ...................... 604/34 |
| 4,636,205 A | | 1/1987 | Steer |
| 4,642,107 A | * | 2/1987 | Arnone et al. ................. 604/342 |
| 4,721,508 A | * | 1/1988 | Burton ............................ 604/338 |
| 4,846,818 A | | 7/1989 | Keldahl et al. |
| 5,045,052 A | * | 9/1991 | Sans ............................... 600/32 |
| 5,170,992 A | * | 12/1992 | Lenberg ........................ 251/304 |
| 5,269,774 A | * | 12/1993 | Gray ............................. 604/343 |
| 5,287,852 A | * | 2/1994 | Arkinstall ............... 128/207.14 |
| 5,372,594 A | | 12/1994 | Colacello et al. |
| 5,501,677 A | * | 3/1996 | Jensen ........................... 604/338 |
| 5,569,216 A | * | 10/1996 | Kim ............................... 604/277 |
| 5,865,820 A | * | 2/1999 | Myello et al. ................. 604/345 |
| 6,497,250 B1 | * | 12/2002 | Johann ..................... 137/625.46 |
| 6,722,624 B1 | * | 4/2004 | Watson et al. .................... 251/78 |
| 6,723,079 B2 | * | 4/2004 | Cline ............................. 604/337 |
| 7,001,367 B2 | | 2/2006 | Arkinstall |
| 7,258,661 B2 | * | 8/2007 | Davies et al. .................... 600/32 |
| 2002/0077611 A1 | | 6/2002 | von Dyck et al. |
| 2004/0181197 A1 | * | 9/2004 | Cline ............................. 604/337 |
| 2007/0123832 A1 | * | 5/2007 | Cline et al. .................... 604/335 |
| 2008/0015405 A1 | * | 1/2008 | Davies et al. .................... 600/32 |
| 2010/0022976 A1 | * | 1/2010 | Weig ............................. 604/355 |

FOREIGN PATENT DOCUMENTS

| | | | |
|---|---|---|---|
| EP | 1 714 626 | 10/2006 | |
| JP | 5122296 | 2/1976 | |
| JP | 04189351 A | 7/1992 | |
| JP | 2007517166 A | 6/2007 | |
| WO | 2008/067603 | 6/2008 | |
| WO | WO 2008067603 A1 | * 6/2008 | ............... F16K 5/06 |
| WO | 2008/103788 | 8/2008 | |
| WO | 2008/152585 | 12/2008 | |
| WO | 2009029610 A1 | 3/2009 | |
| WO | 2009/155537 | 12/2009 | |

OTHER PUBLICATIONS

International Search Report for International Application No. PCT/AU2011/000094, International Preliminary Examining Authority/Australia, mailed Apr. 21, 2011, 6 pages.

Office Action, China Serial No. 201180017409.9, Mar. 19, 2014, 14 pages.

Khubchandani, I.T., et al., "The Magnetic Stoma Device: A Continent Colostomy," Dis Colon Rectum 1981; 24:344-350.

Written Opinion, Singapore Application No. 201205651-1, Jan. 16, 2014, 10 pages.

Patent Examination Report, Australia Application No. 2011208954, Feb. 28, 2014, 5 pages.

Extended European Search Report, EP11736546.0, Jun. 6, 2014, 5 pages.

Supplementary European Search Report, EP11736546.0, May 28, 2014, 4 pages.

Office Action, Japanese Patent Application No. 2012-550268, Nov. 26, 2014, 6 pages.

Office Action, Chinese Patent Application No. 201180017409.9, Dec. 23, 2014, 8 pages.

* cited by examiner

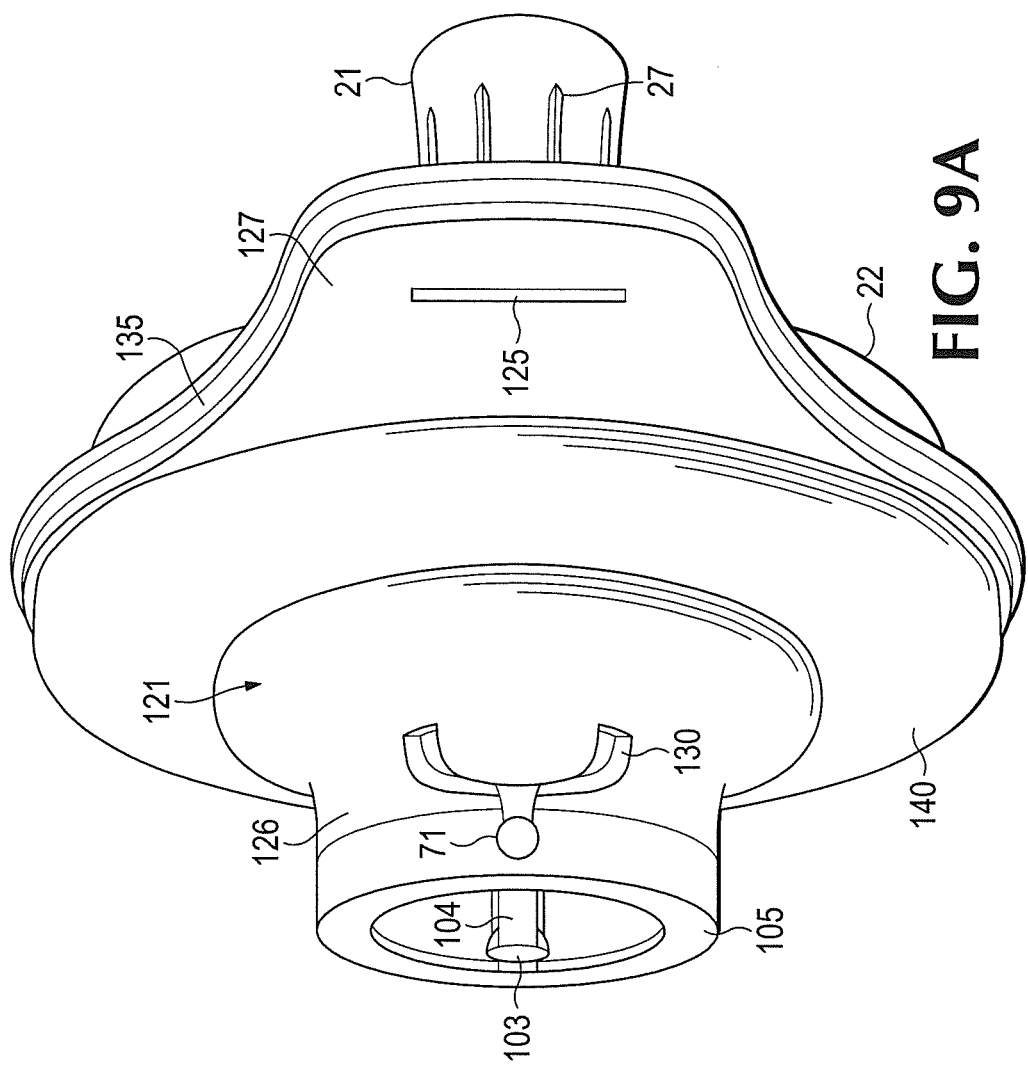
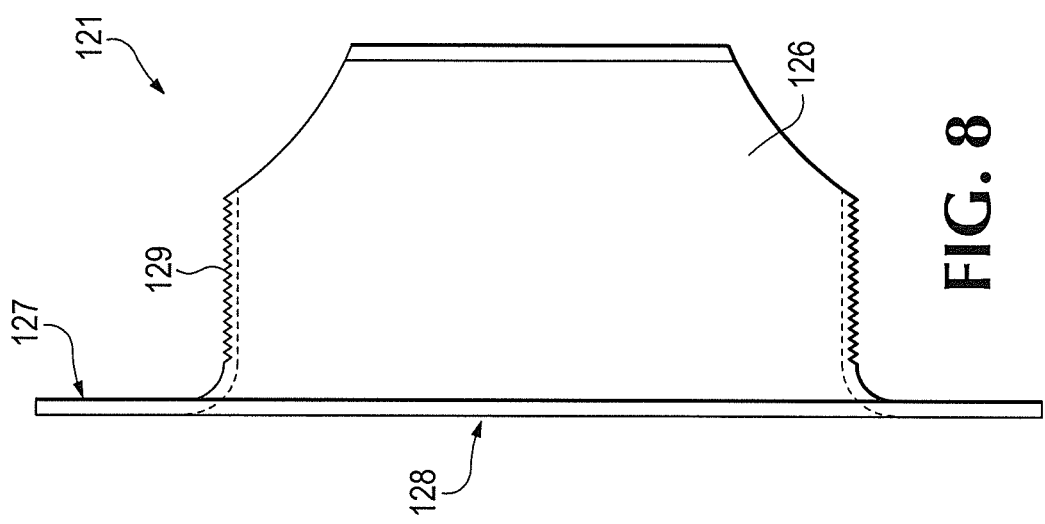

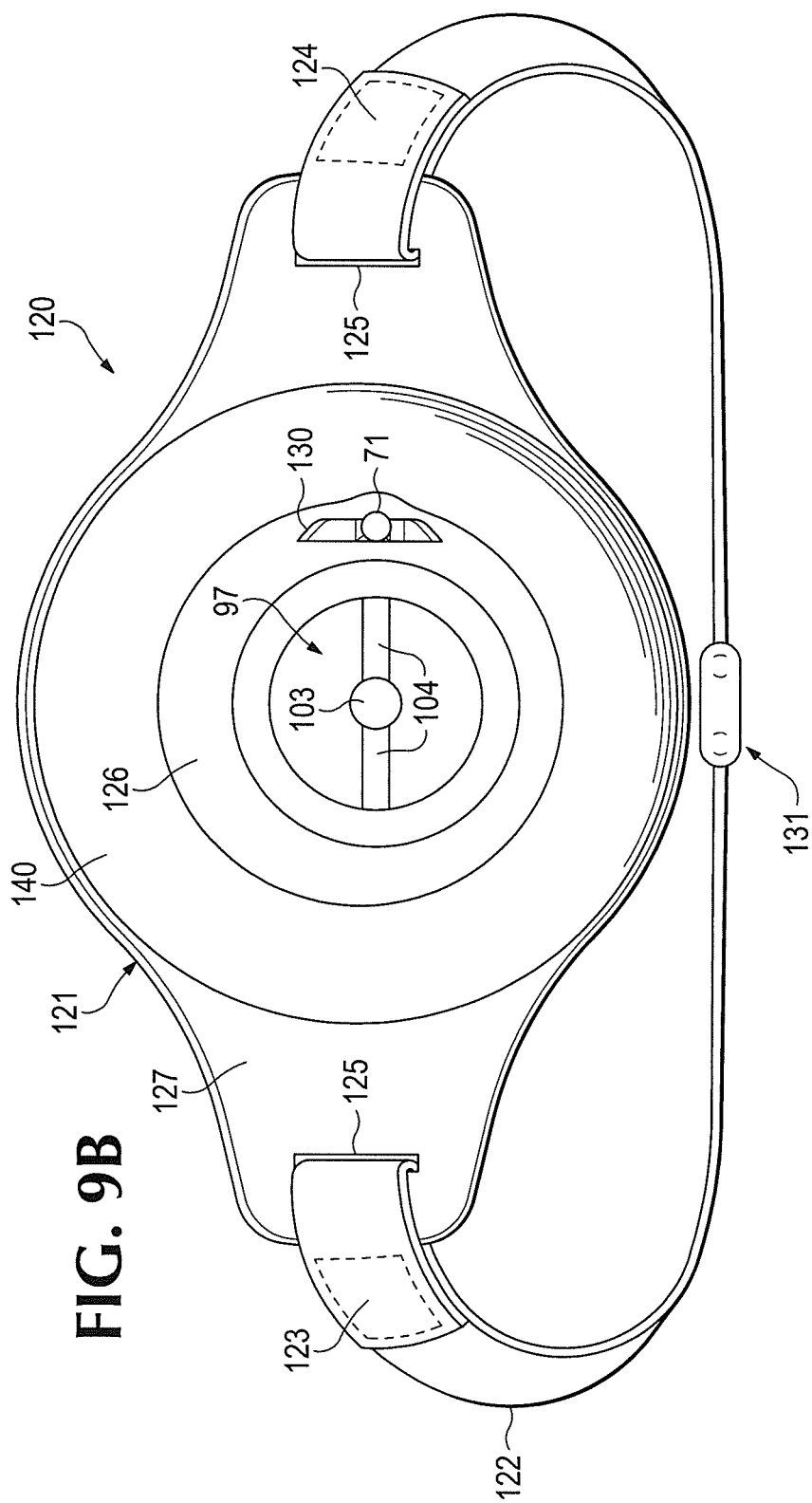

MEDICAL DEVICE

CROSS-REFERENCE TO RELATED PATENT APPLICATIONS

This application is a continuation of International Application No. PCT/AU2011/000094, filed Feb. 1, 2011 which claims priority to AU 2010900379 filed Feb. 1, 2010, both of which are herein incorporated by reference in their entirety.

FIELD OF THE INVENTION

Throughout this specification, unless the context requires otherwise, the word "comprise" and variations such as "comprises", "comprising" and "comprised" will be understood to imply the presence of a stated integer or group of integers but not the exclusion of any other integer or group of integers.

The headings in this specification are provided to assist the reader, and are not to be interpreted so as to narrow or limit the scope of the disclosure in the description, claims or drawings.

The present invention relates to a medical device.

In particular, the present invention relates to an ostomy device. The ostomy device of the present invention is used by people who have undergone an ostomy procedure, such as a colostomy or an ileostomy.

An ostomy procedure may be carried out, for example, when the intestine (the large intestine or the small intestine) of a patient is affected by disease (e.g. colon cancer), trauma (e.g. serious abdominal injury) or intestinal surgery, and results in the patient losing the normal function in which waste material, i.e. faeces, is discharged from the body via the anus. An ostomy procedure replaces the loss of the normal waste elimination function.

In an ostomy procedure, the intestine of a patient is cut. Depending upon the reason for the ostomy procedure, the cut may be to the large intestine, i.e. the colon, or to the small intestine (in this case, usually at the end of the ileum). The cut end of the intestine, that is still in communication with the stomach, is drawn through an incision made in the abdominal wall of the patient. The end of the intestine is then sutured to the skin on the outside of the incision to form a stoma. Intestinal waste, i.e. faeces, then exits the person's body via the stoma and the normal function of the anus to discharge faeces ceases.

When the ostomy procedure is performed to create the stoma using the large intestine, i.e. the colon, the procedure is known as a colostomy. When the ostomy procedure is performed to create the stoma using the small intestine, the procedure is known as an ileostomy.

An ostomy procedure may be temporary or permanent. Whether the ostomy procedure performed is temporary or permanent will depend upon the reason that the ostomy procedure is being performed.

A temporary ostomy may be performed, for example, when surgery is performed on the colon and the colon requires time to rest and heal. In such circumstances, the portion of the colon being rested is closed off and waste discharge is via the stoma. Once the colon has healed, the portion of the colon used to form the stoma is reconnected with the portion of the colon that was rested and the stoma closed. The patient is then able to resume normal waste elimination function via the anus. A temporary ostomy, for example, may last from a few weeks to several months.

A permanent ostomy may be performed, for example, when a serious disease, such as colon cancer, has affected the colon. In such circumstances, the diseased part of the colon is removed and a stoma is formed for waste discharge. Any remaining part of the colon connecting to the anus is closed off and normal waste elimination function via the anus ceases for the duration of the life of the patient.

Whilst the stoma provides an opening to allow waste to exit the body, the stoma has none of the functions of the anus and the sphincter in controlling the exit of waste. Thus, after an ostomy has been performed on a person, waste material exits the intestine through the stoma. This process is involuntary, the person having no control over the process.

Consequently, once an ostomy has been performed on a person it is necessary that provision is made to cater for the loss of the normal waste elimination function.

BACKGROUND ART

The discussion of the background art, any reference to a document and any reference to information that is known, which is contained in this specification, is provided only for the purpose of facilitating an understanding of the background art to the present invention, and is not an acknowledgement or admission that any of that material forms part of the common general knowledge as at the priority date of the application in relation to which this specification was filed.

Following an ostomy procedure, it is commonplace that an ostomy bag is used to collect the intestinal waste that exits from the stoma. The opening of the ostomy bag is attached directly to the skin, of the person, around the stoma. The bag is attached to the skin with adhesive. The person must empty and replace the bag as necessary. The frequency of replacement of the bag varies, though is often between once and several times a day.

Replacement of the bag requires that first the adhesive attachment to the skin is broken and the existing bag removed. The existing bag and its contents must be disposed of appropriately. The person must clean the stoma and the skin around the stoma. This is very important to reduce the risk of serious problems arising, including infection and necrosis of the stoma. There are various preparations that the person must constantly use to maintain the site of the stoma clean. As intestinal waste passes out through the stoma, it comes into direct contact with the stoma. Thus, the person must follow the cleaning regimen each time a bag is removed and replaced with a new one, which may be required several times a day. Once the site of the stoma has been cleaned, the person attaches a new bag to the skin around the stoma using adhesive.

In addition, to the problems that can arise if the stoma is not maintained clean, the constant application of adhesive to skin around the stoma, to attach the bag, leads to skin irritation, skin rashes and pealing skin.

Furthermore, the person is constantly confronted with the unpleasant odour that is attendant to having a stoma for discharge of intestinal waste.

People who must live with having a stoma and using an ostomy bag can suffer tremendous hardship. Some of the problems and inconvenience of dealing with their condition have been hereinbefore described. In addition, they often suffer deterioration in their personal, family, social and employment relationships. This can lead to other problems and conditions, including loss of self-esteem, a sense of isolation, depression and suicide.

DISCLOSURE OF THE INVENTION

In accordance with one aspect of the present invention, there is provided an ostomy device comprising an implant arranged, in use, to be located inside the body of a person near the site of a stoma, discharge means arranged, in use, to provide means for intestinal waste to exit to the exterior of the body of the person, and means, in use, to be operatively associated with the implant and removably retain the discharge means at the site of the stoma.

Preferably, in use, the discharge means is removably retained at the site of the stoma by magnetic force.

The means, in use, to be operatively associated with the implant and removably retain the discharge means at the site of the stoma may comprise retention means.

Preferably, the implant and the retention means are magnetically attracted.

The retention means may comprise a retention member. The retention member may be a ring or annular disc.

Alternatively, or in addition, the retention means may comprise at least a portion of the discharge means. This portion of the discharge means may be an annular disc or flange member.

Preferably, the implant is flexible.

Preferably, the implant is substantially in the form of an annular disc.

Preferably, the discharge means comprises a tubular member, and a portion of the tubular member is arranged, in use, to be located in the intestine that is used to form the stoma.

Preferably, the discharge means comprises an annular disc, or flange member, at substantially one end of the tubular member and is arranged, in use, to bear against the body of the person near the site of the stoma when the tubular member is located in the intestine of the person.

Preferably, the discharge means is provided with valve means to control the discharge of intestinal waste to the exterior of the body of the person.

Preferably, the discharge means comprises a first portion and a second portion detachably connected together, the fist portion having the tubular member and the second portion having the valve means.

Preferably, securing means is provided, in use, to secure the discharge means at the site of the stoma.

Preferably, the ostomy device further comprises case means arranged, in use, to be provided between the retention means and the site of the stoma and substantially cover the second portion of the discharge means.

Preferably, the retention means is arranged to be removably mounted to the case means.

In accordance with another aspect of the present invention, there is provided an ostomy insertion device comprising a tubular member having a first end arranged, in use, to insert the tubular member into the body of a person, flange means provided at the region of a second end of the tubular member spaced from the first end of the tubular member, the flange means provided with a recess therein adjacent the second end of the tubular member, and an annular plate portion adjacent the recess, wherein, in use, the recess is located substantially aligned over a stoma of the person and the annular plate portion bears against the body of the person around the site of the stoma.

Preferably, the ostomy insertion device further comprises a bladder provided in the recess such that, in use, the bladder is inflatable to seal around the site of the stoma.

Preferably, an inlet is provided in the flange means, in use, for injecting air into the bladder to suitably inflate the bladder.

Preferably, the tubular member is provided with stiffening means to provide the tubular member with a degree of rigidity.

BRIEF DESCRIPTION OF THE DRAWINGS

The present invention will now be described, by way of example only, with reference to the accompanying drawings, in which:

FIG. 8 is a side view of the securing belt, of the ostomy device shown in FIG. 1, with the strap omitted;

FIG. 9A is a perspective view of the securing belt, shown in FIG. 8, in position over the discharge unit of the ostomy device shown in FIG. 1;

FIG. 9B is a plan view of the securing belt, including the strap, shown in FIG. 9, in position over the discharge unit of the ostomy device shown in FIG. 1;

BEST MODE(S) FOR CARRYING OUT THE INVENTION

Figure 1:
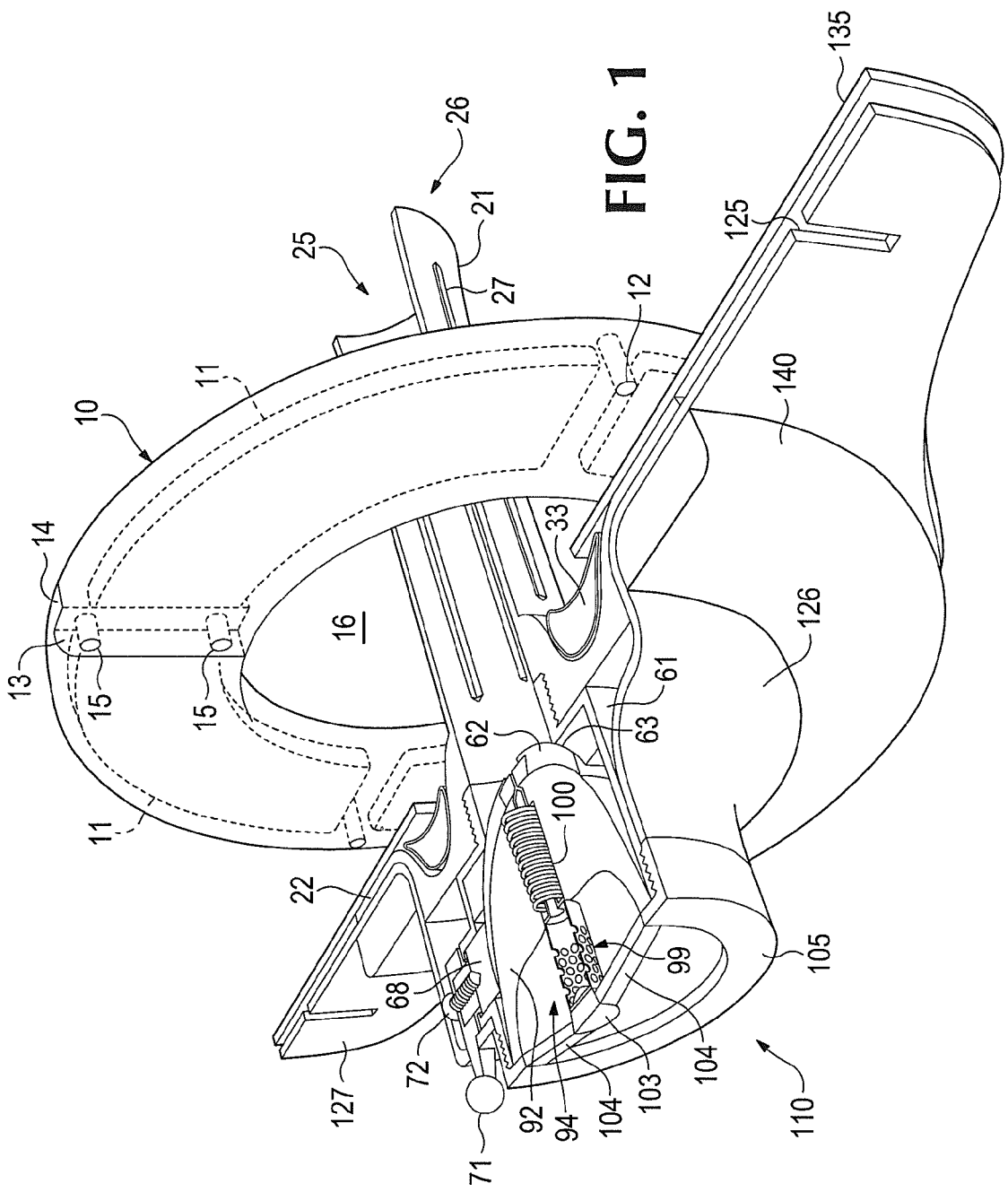
FIG. 1 is a partially cutaway perspective view of an embodiment of an ostomy device in accordance with one aspect of the present invention.
Figure 12:
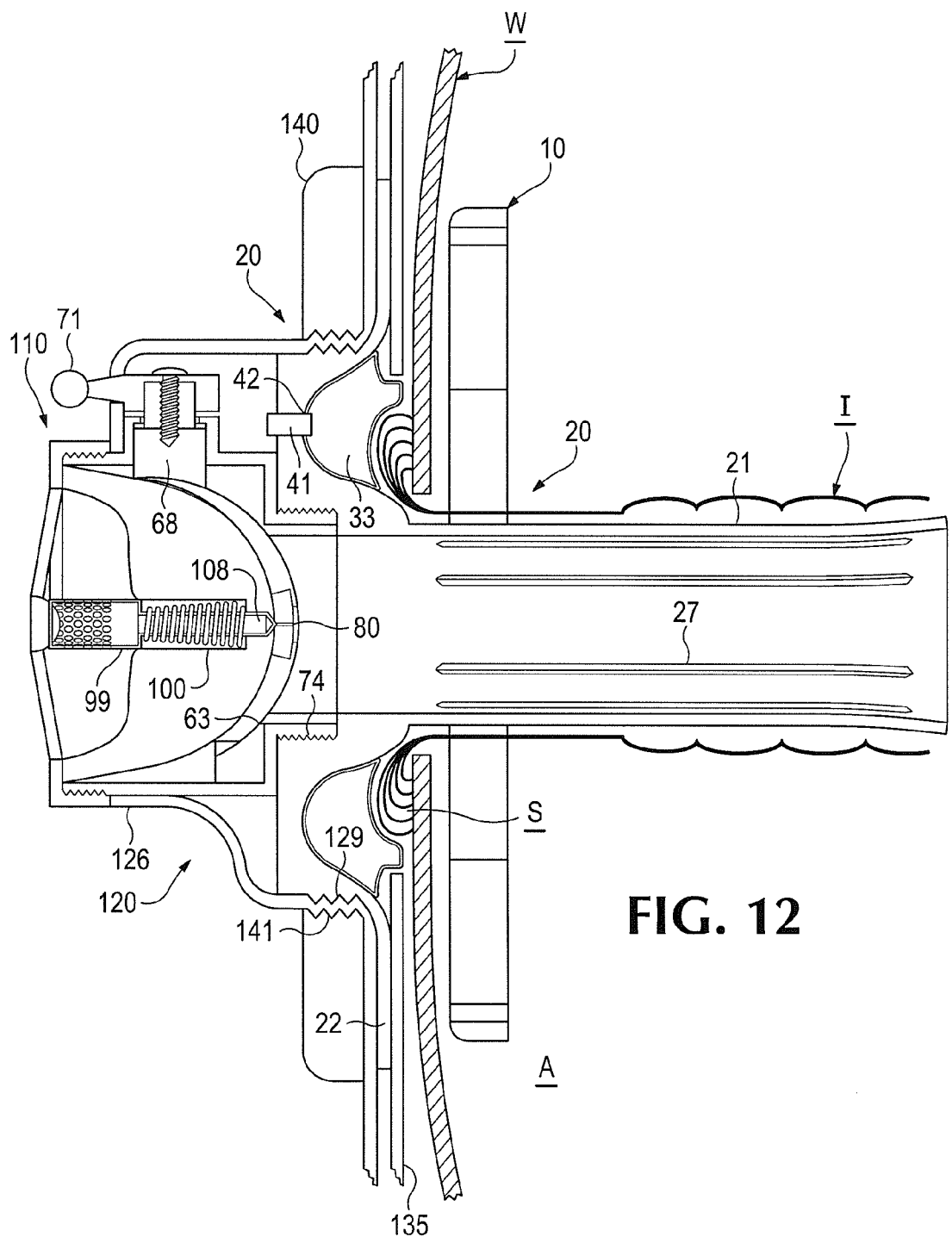
FIG. 12 is a cross-sectional view showing the implant situated inside the body of the person near the site of the stoma and the discharge device located at its position at the stoma.

FIGS. 1 and 12 show an embodiment of an ostomy device 1. For clarity of presentation, not all of the features of the ostomy device 1 have been identified by a reference numeral in FIGS. 1 and 12. However, the components and features of the embodiment of the ostomy device 1 of the present invention are illustrated and identified by reference numerals in the other accompanying drawings.

The ostomy device 1 of the present invention comprises an implant 10 arranged, in use, to be located inside the body of a person near the site of a stoma S, a discharge device 20 is arranged, in use, to provide means for intestinal waste to exit to the exterior of the body of the person, and retention means, in use, to be operatively associated with the implant 10 and removably locate and retain, the discharge device 20 at the site of the stoma S, i.e. so that it is positioned and retained at the site of the stoma S.

In use, the discharge device 20 is retained at its location at the site of the stoma S by magnetic force, i.e. magnetic attraction, as will be further described herein.

The retention means, in use, to be operatively associated with the implant 10 and removably retain the discharge means 20 at the site of the stoma S may comprise a retention ring 140. The implant 10 and the retention ring 70 are magnetically attracted.

The retention means, in use, to be operatively associated with the implant 10 and removably retain the discharge means 20 at the site of the stoma S may, alternatively or additionally, comprise a portion of the discharge device 20. This portion of the discharge device 20 may be an annular disc, or flange member, 22.

The components of the embodiment of the ostomy device 1 of the present invention will be described herein in detail followed by a description of how they are used.

Implant

Figure 2B:
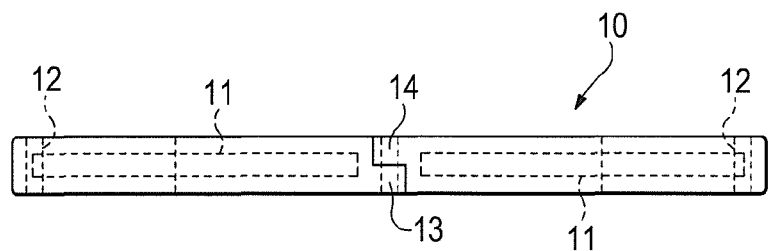
FIG. 2B is a top plan view of the implant shown in FIG. 2A.
Figure 2A:
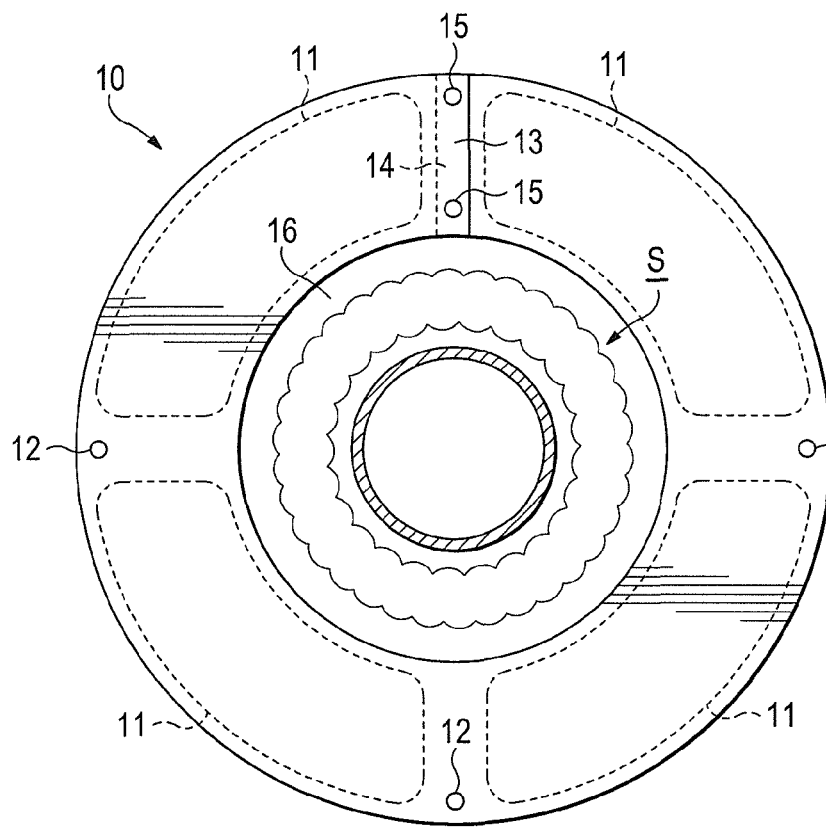
FIG. 2A is an elevation view of the implant, of the ostomy device shown in FIG. 1, which, in use, is situated inside the body of a patient.
Figure 2C:
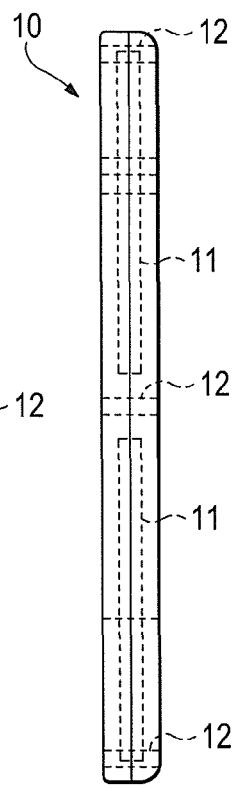
FIG. 2C is a side view of the implant shown in FIG. 2A.
Figure 3:
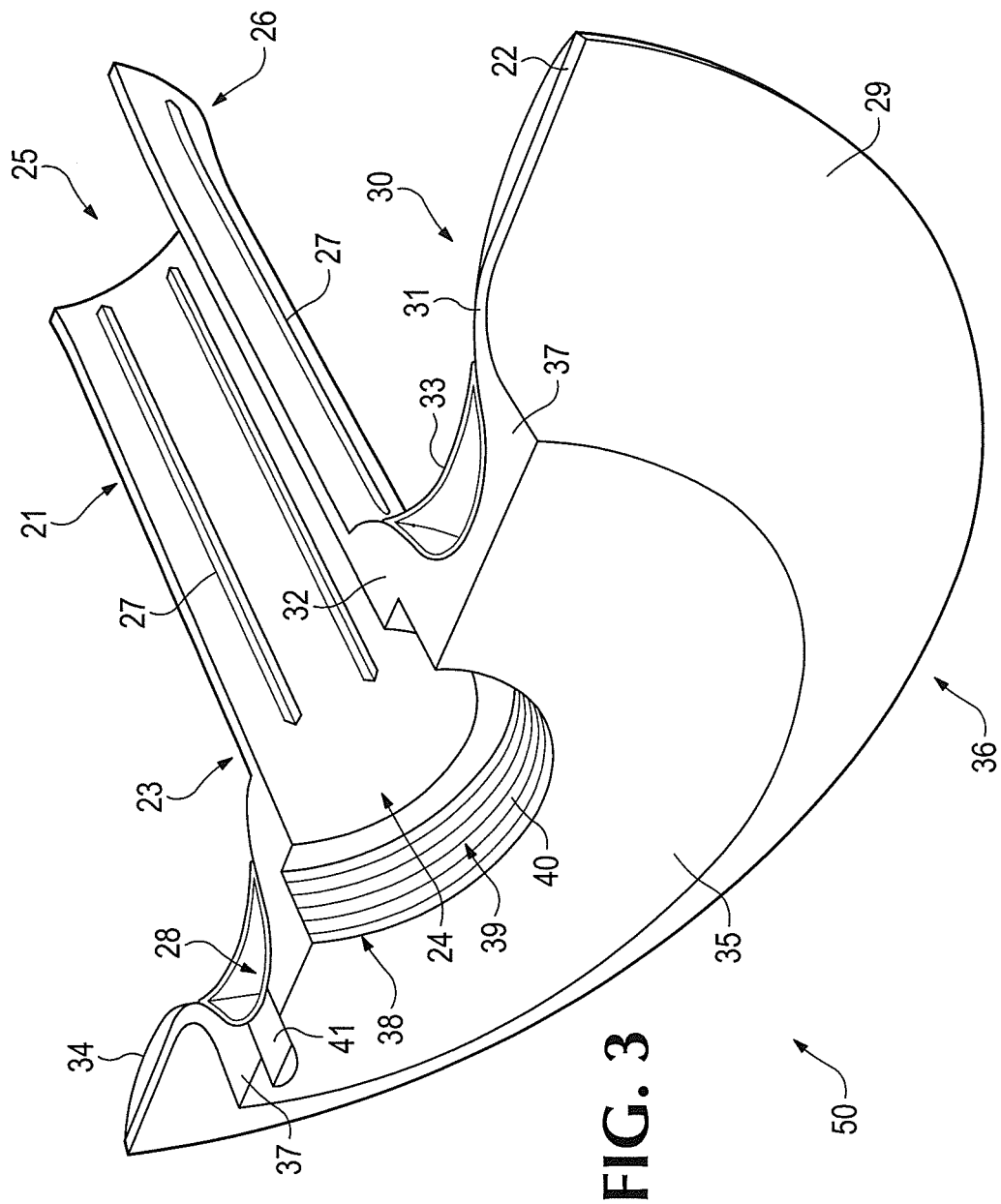
FIG. 3 is a first perspective cutaway view of the insertion unit of the discharge device, of the ostomy device, shown in FIG. 1.
Figure 4:
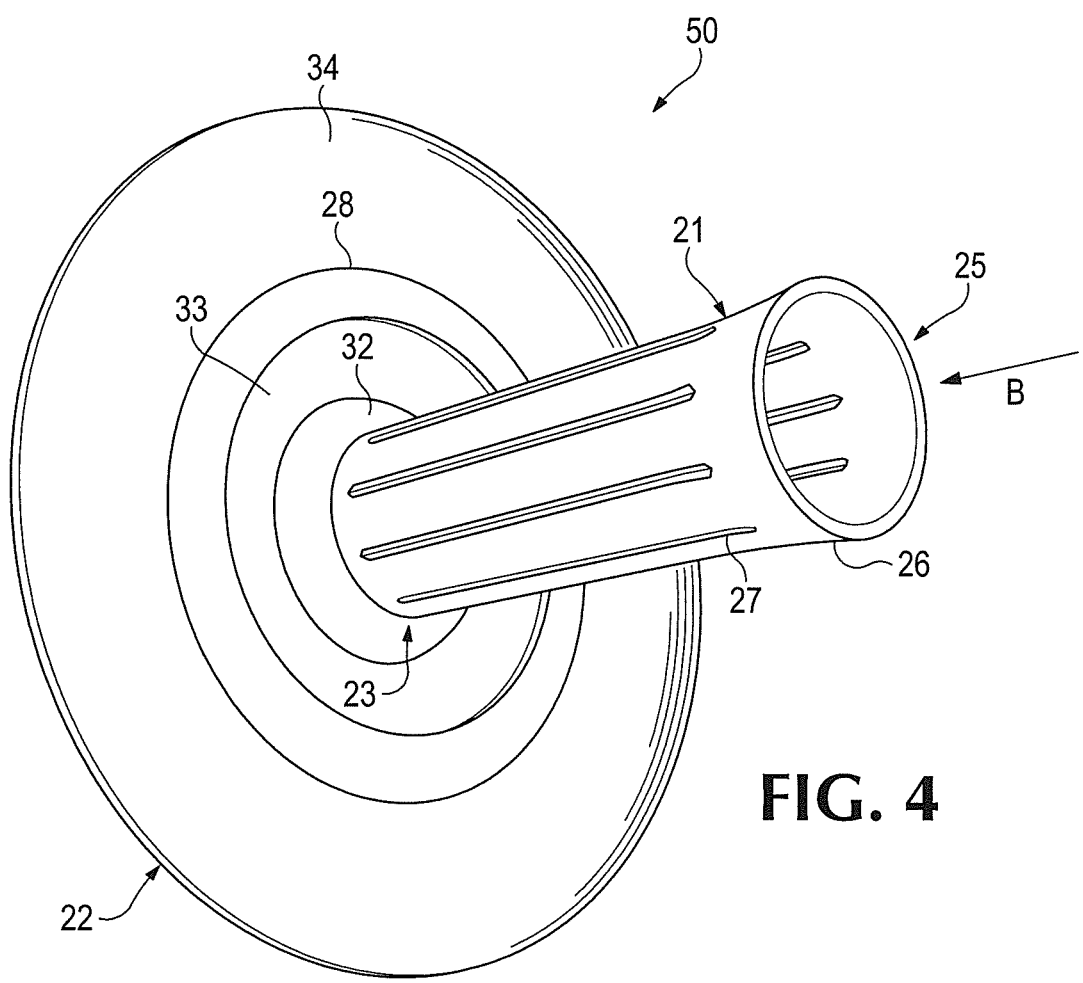
FIG. 4 is a second perspective view of the insertion unit, shown in FIG. 3.
Figure 5A:
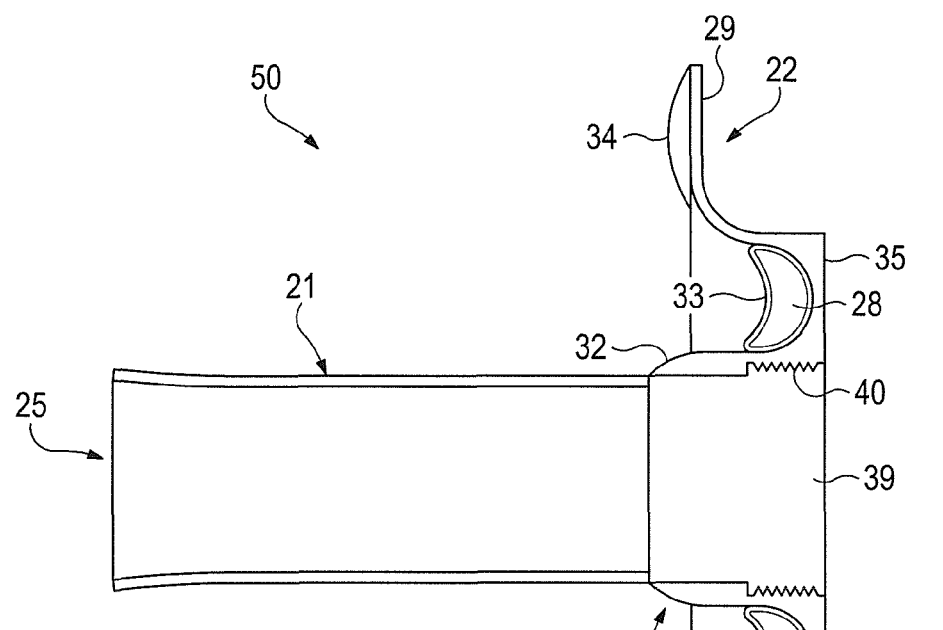
FIG. 5A is side cross sectional view of the insertion unit shown in FIGS. 3 and 4.
Figure 5B:
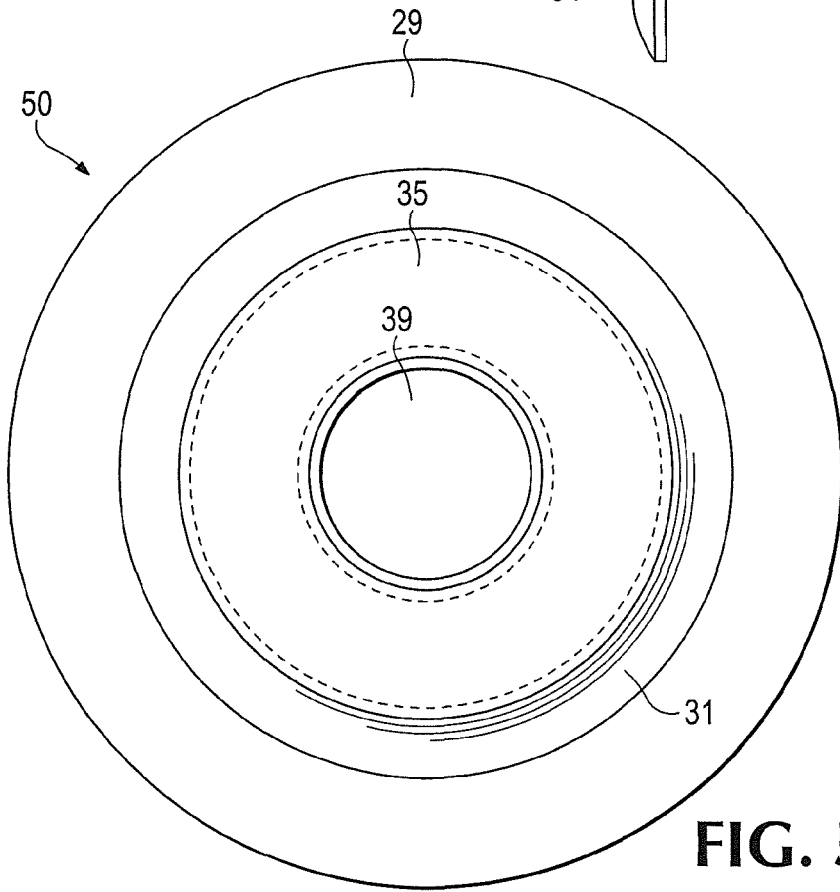
FIG. 5B is a front elevation view of the insertion unit, shown in FIGS. 3 and 4, in the direction shown by arrow B in FIG. 4.

FIGS. 2A, 2B and 2C show an embodiment of an implant 10, which, in use, is arranged to be positioned inside the body of a person adjacent the site of a stoma S, as will be further described herein. The person is a patient who has undergone an ostomy procedure.

The implant 10 is magnetised so that it creates a magnetic field. This may be done, for example, by embedding or impregnating the implant 10 with magnetised material 11, illustrated by the broken lines in FIGS. 2A, 2B and 2C. In an alternative example, the implant 10 may be made entirely of magnetised material.

The implant 10 is flexible. It can be bent and can conform to the contours of the abdominal wall of the person at the site at which it is sutured to the abdominal wall. The implant 10 is provided with holes 12 so that it can be sutured to the abdominal wall inside the body of the person.

The implant 10 may be provided in the form of an annular disc or ring with flat opposed faces, as shown in FIGS. 2A, 2B and 2C. The implant 10 is not continuous. Instead, the implant 10 is connected at respective end regions 13 and 14 by pins 15 after the implant 10 has been inserted into the body of the person. Each end region 13 and 14 is provided with a cut-out portion. These cut-out portions abut and overlap to form the completed ring. The pins 15 are then inserted into and located in aligned holes provided in the abutting and overlapped cut-out portions to thereby connect together the respective end regions 13 and 14 of the implant 10.

An alternative to the use of pins 15 to connect together the respective end regions 13 and 14 is to have complementary press studs located at the respective cut-out portions at the end regions 13 and 14. The press studs may be moulded integrally with the implant 10. The end regions 13 and 14 can then be connected together by pressing the complementary studs into engagement.

The implant 10 has a central opening 16.

The thickness of the implant is substantially less that its overall diameter. The implant 10 is dimensioned for the type of ostomy for which it will be used. For example, in the case of an ileostomy the implant 10 may have an inner diameter, i.e. the diameter of the opening 16, of approximately 3.5 cm to 4.0 cm, an outer diameter of approximately 7.0 cm to 8.0 cm and a thickness of approximately 3 mm.

Discharge Device

The discharge device 20 and its component parts are shown in FIGS. 3 to 7B. The discharge device 20 is arranged, in use, to provide means for intestinal waste to exit from the intestine of the person via the stoma S and be discharged to the exterior of the body of the person. The discharge of the intestinal waste can occur in a controlled manner.

Ostomy Insertion Device

The discharge device 20 comprises a tubular member 21, and a flange, or annular disc, member 22. The flange member 22 is provided at an end 23 of the tubular member 21, around an end 23 of the tubular member 21. The tubular member 21 has an opening 24 at the end 23. The tubular member 21 has another opening 25 at its other end 26. The tubular member 21 is provided with ribs 27. The ribs 27 extend in the longitudinal direction of the tubular member 21, at spaced intervals around the circumference of the tubular member 21. The ribs 27 may be imbedded with the tubular member 21. The ribs 27 provide the tubular member 21 with a degree of rigidity.

The flange member 22 has a recess portion, or trough, 28 and an outer portion 29. The recess portion 28 is concave shaped and extends around the end 23 of the tubular member 21 in a substantially circular manner. The outer portion 29 surrounds the recess portion 28. The outer portion 29 is substantially flat and in the form of substantially an annular plate. The recess portion 28 is provided on a first side 30 of the flange member 22. The first side 30 is arranged, in use, to face the skin of the person at the site of the stoma S. A curved portion 31 of the flange member 22 connects the outermost portion of the recess 28 with the outer portion 29.

The region of the flange member 22 at its juncture with the tubular member 21 forms a hub 32. The recess portion 28 is provided between the outer portion 29 and the hub 32, at the first side 30 of the flange member 22.

A bladder 33 is located in the recess portion 28. The bladder 33 is annular, or doughnut, shaped. The bladder 33 is inflatable.

The outer portion 29 of the flange member 22 is provided with cushioning material 34 on the first side 30 of the flange member 22. The cushioning material 34 may be provided over substantially the entire surface of the outer portion 29 at the first side 30 of the flange member 22. The cushioning material 34, being on the first side 30 of the flange member 22 which faces the skin of the person at the site of the stoma S, provides cushioning comfort to the person.

The flange member 22 has a rear, or abutment, surface 35 on the second side 36 of the flange member 22. The abutment surface 35 is substantially flat. The second side 36 of the flange member 22 is opposed to the first side 30. The abutment surface 35 is opposed to the recess 28. The abutment surface 35 is spaced from the outer portion 29 at the first side of the flange member 22 by the curved portion 31 and the outer part of a projecting section 37 of the flange member 22 formed on the second side 36.

The inner part 38 of the projecting portion 37 defines an opening 39. The opening is aligned with the opening 24 of the tubular member 21. In this way, a continuous passage is formed from the opening 25 through the tubular member 21 to the opening 39. A screw thread 40 is provided at the inner part 38 of the projecting portion 37.

An inlet 41 extends through the projecting portion 37 from the abutment surface 35 to the recess 28. The bladder 33 has an opening 42 (best seen in FIG. 12) therein which is attached to the inlet 41 at the recess 28 whereby the bladder 33 is in communication with the inlet 41 such that the bladder 33 may be inflated.

The tubular member 21 is arranged, in use, to be inserted into the stoma S of the person such that it is positioned in the intestine I of the person. The flange member 22, in use, is located outside the body of the person, whereby the flange member 22 bears against the body of the person around the site of the stoma S, as will be later herein described.

The features of the discharge device 20 as described so far herein form an ostomy insertion device 50.

Discharge Control Device

The discharge device 20 further comprises a valve 60. The valve 60 is provided in a housing 61, as can be best seen in FIGS. 6A and 6B. The housing 61 is substantially in the form of a short tube.

The valve 60 comprises a sealing member, or valve member, 62, and a valve seat 63. The valve seat 63 is formed by an internal surface of the housing 61. The sealing member 62 has a substantially convex surface 64 and a substantially concave surface 65. The convex surface 64 and the concave surface 65 are provided on opposed faces of the sealing member 62. The sealing member 62 is partly substantially spherical, being a part of a segment of a sphere. The segment extends through substantially 180 degrees about a first axis from a first axial side 66 to a second axial side 67. The segment extends through to substantially 90 degrees about a second axis orthogonal to the first axis.

The sealing member 62 is rotatably mounted in the housing 61. A shaft 68 extends from the convex surface 64 of the sealing member 61 adjacent the first axial side 66. The shaft 68 is rotatable about an axis 69. The shaft 68 is rotatably accommodated in a socket 70 extending outward from the housing 61. A handle 71 is operatively connected with the shaft 68 by a fastener, such as a screw 72. The screw 72 passes through the handle 71, an intermediate connector 73 and onto the end of the shaft 68.

The housing 61 is provided with a neck 74 at one end thereof. The diameter of the neck 74 is less than the diameter of the portion of the housing 61 that accommodates the sealing member 62. The neck 74 is provided with a screw thread 75 on its external surface. A screw thread 76 is provided on the external surface of the housing 61 at the end of the housing 61 spaced from the neck 74. The housing 61 is provided with an opening 77 at the end of the neck 74 and another opening 78 at the end of the housing 61, spaced from the neck 74, near which the screw thread 76 is provided. The sealing member 62 is provided between the neck 74 and the opening 78.

An annular surface 79 is formed between the neck 74 and the remainder of the housing 61 which is of greater diameter than the neck 74.

A narrow hole 80 is provided at the apex region 81 of the sealing member 62. The apex region 81 of the sealing member 62 is formed of a compressible material. The hole 80 is normally closed due to the compressive force exerted by the compressible material.

Figure 7A:
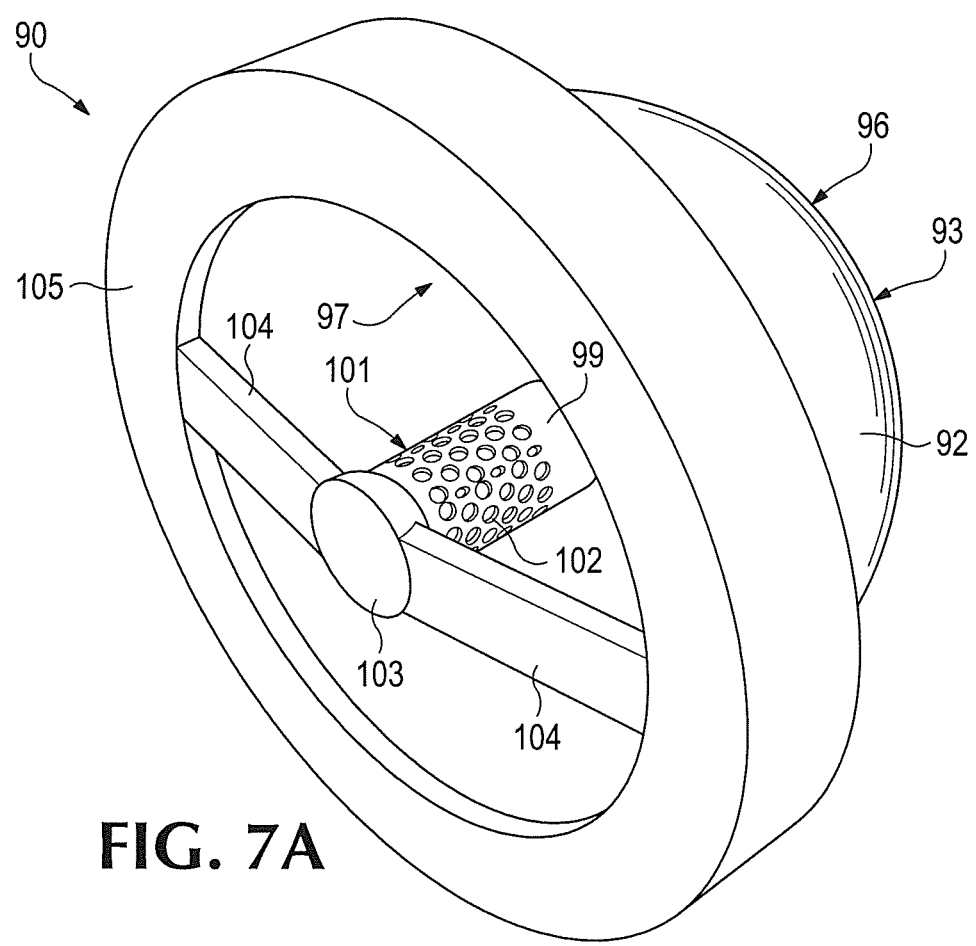
FIG. 7A is a perspective view of the closure cap for the discharge control valve housing.
Figure 7B:
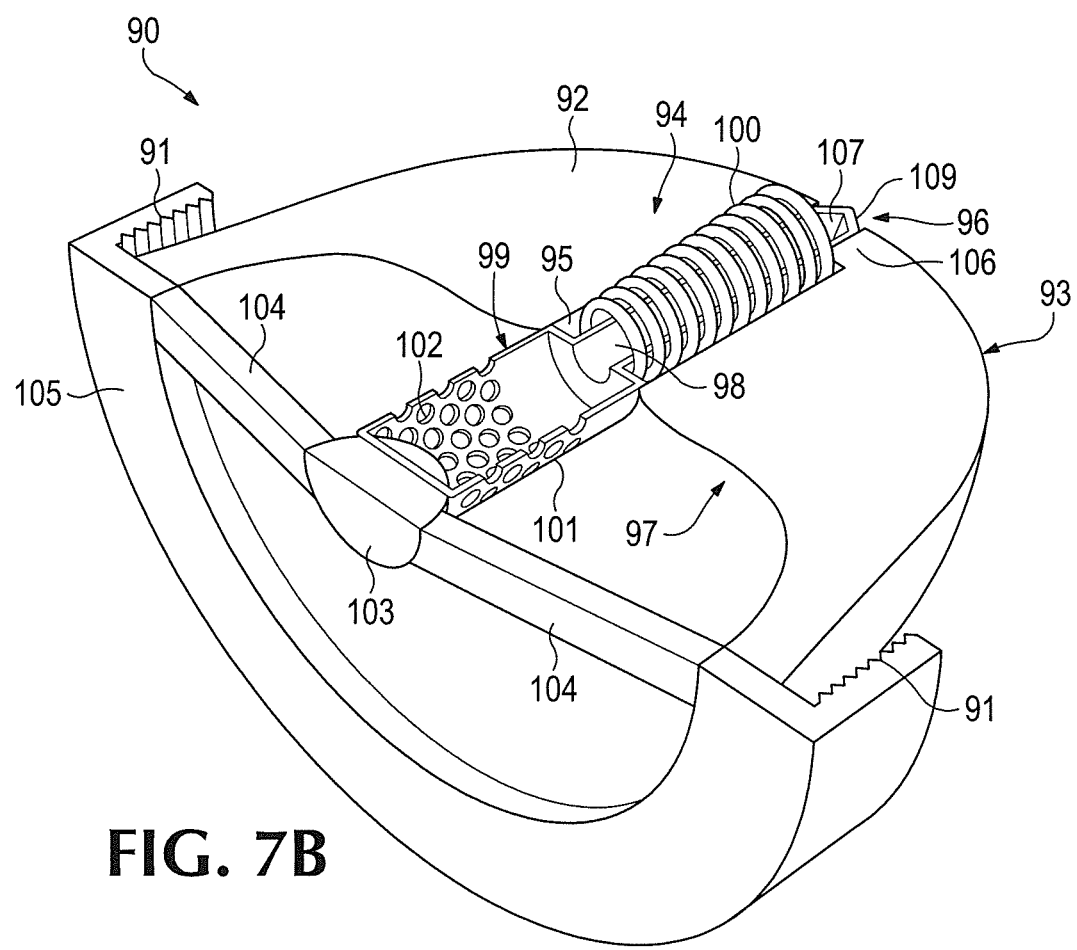
FIG. 7B is a cutaway second perspective view of the closure cap for the discharge control valve housing

A cap 90 is provided to close the opening 78 of the housing 61. The cap 90 is shown in FIGS. 7A and 7B. The cap 90 is provided with a screw thread 91. The screw thread 91 can engage with the screw thread 76 on the housing 61 to thereby securely, yet detachably, fix the cap 90 to the housing 61.

The cap 90 is provided with a projection, or extension, 92 that extends into the housing 61 when the cap 90 is screwed onto the housing 61. The projection 92 is substantially dome shaped and has a convex surface 93. The convex surface 93 is shaped to substantially conform to the shape of the convex surface 65 of the sealing member 62.

The cap 90 accommodates a pressure release valve 94, part of which is accommodated by the projection 92. The projection 92 is provided with a hole 95 therethrough. The hole 95 extends through the projection 92 from the apex region 96 to the outer side 97 of the projection 92. When the cap 90 is screwed onto the housing 61, the apex region 96 is located inside the housing 61 and the outer side 97 is located outside the housing 61. A narrow portion 98 of a tube 99 is located in the hole 95. A spring 100 is provided around the narrow portion 98. The tube 99 has a wider portion 101 located outside the hole 95 at the outer side 97 of the projection 92. The wider portion 101 is provided with apertures 102. A button 103 closes the end of the wider portion 101 of the tube 99. Spokes 104 extend from the button 103 to the rim 105 of the cap 90. The spokes 104 keep the tube 99 in substantially axial alignment with the hole 95. The spokes 104 are substantially rigid but are able to flex so that the button 103 can be depressed against the biasing action of the spring 100. One end of the spring 100 abuts against the end of wider portion 101 that joins the narrower portion 98 of the tube 99. The other end of the spring 100 abuts a ledge 106 formed in the hole 95 near the apex region of the projection 92. A tip 107 at the end of the narrow portion 98 extends beyond the end of the spring 100. The tip 107 is provided with an opening 108 (best seen in FIG. 12). The tip 107 is located in an opening 109 in the apex region 96 of the projection 92.

The features of the discharge device 20 as described under this section form a discharge control device 110.

The ostomy insertion device 50 and the housing 61 can be connected together by engaging the screw thread 75, around the neck 74 of the housing 61, with the screw thread 40 of the ostomy insertion device 50. When the ostomy insertion device 50 and the housing 61 are connected together, the abutment surface 35 of the ostomy insertion device 50 and the annular surface 79 of the housing 61 abut.

Figure 6A:
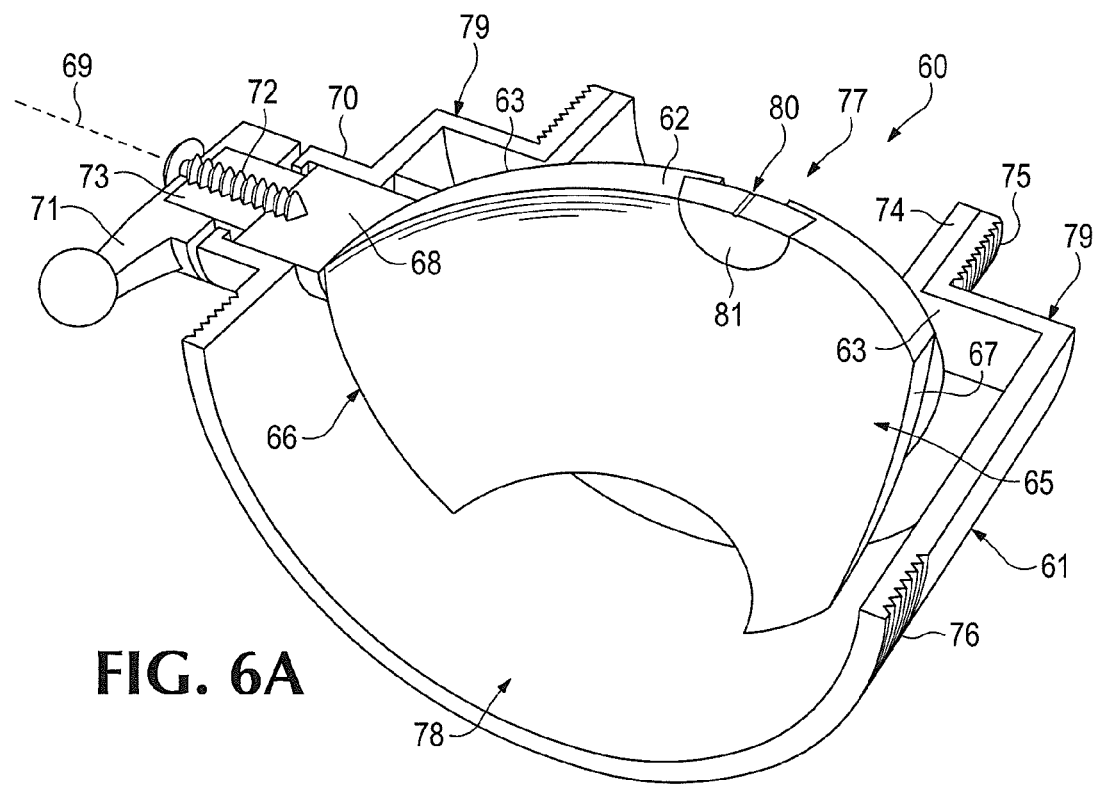
FIG. 6A is a first cutaway perspective view of the discharge control valve and housing showing the valve in its closed condition.

The sealing member 62 is rotatable in the housing 61 by turning the handle 71. In particular, the sealing member 62 is rotatable between a first position and a second position. In the first position, the convex surface 64 is in contact with the valve seat 63. This is the closed condition of the valve 60 and is shown in FIG. 6A and also FIGS. 1 and 12. In the closed condition of the valve 60, fluid cannot pass from the tubular member 21 into the housing 61 beyond the neck 74. The handle 71 may be rotated through substantially 90 degrees to thereby rotate the sealing member 62 to its second position.

Figure 6B:
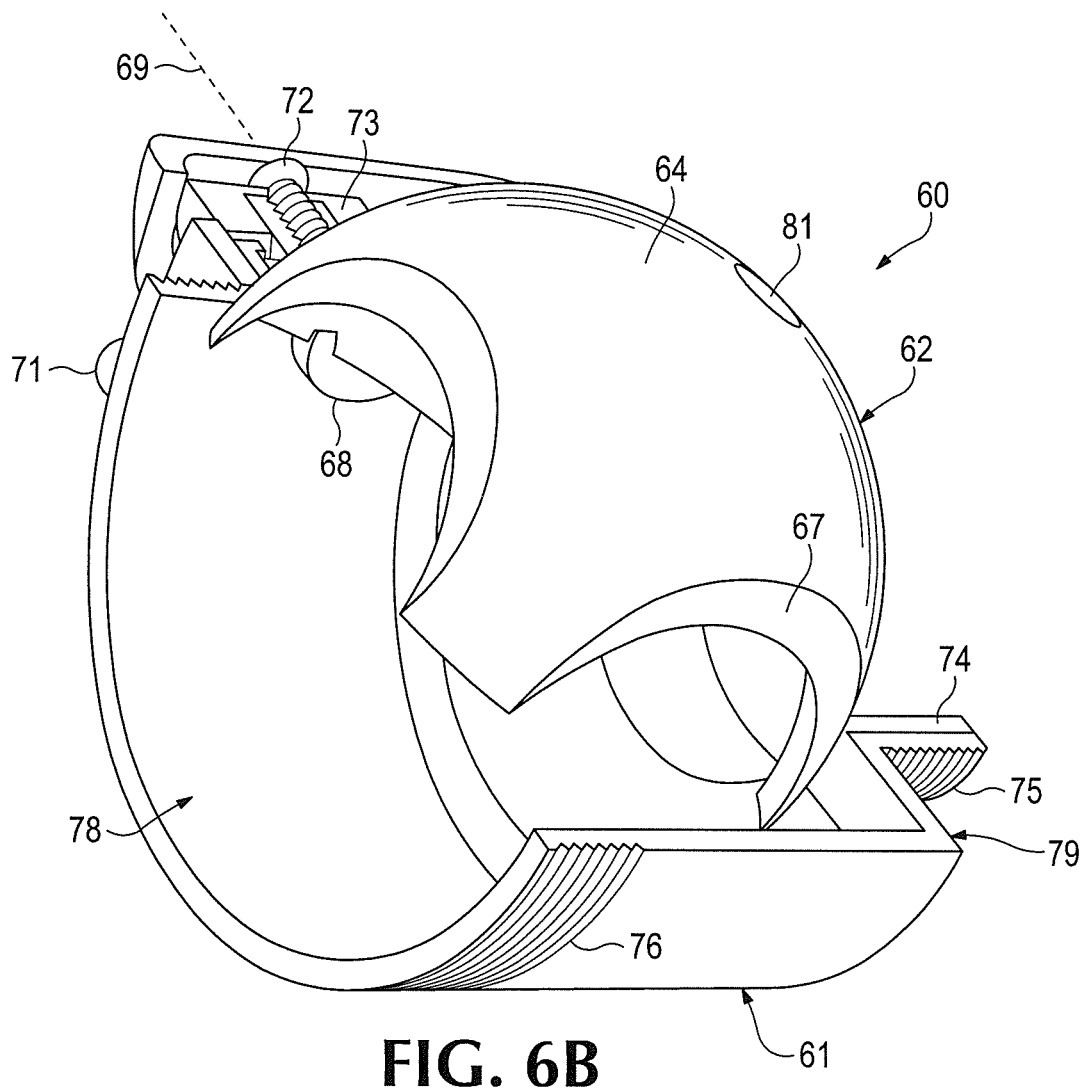
FIG. 6B is a second cutaway perspective view of the discharge control valve and housing showing the valve in its open condition.

In the second position of the sealing member 62, the convex surface 64 is positioned adjacent the inner surface of the housing 61 and is no longer in contact with the valve seat 63. The concave surface 65 also does not obstruct fluid flow such that the second position of the sealing member 62 allows fluid communication between the tubular member 21 and the housing 61. This is the open condition of the valve 30 and is shown in FIG. 6B. Fluid is able to pass from the tubular member 21 into the housing 61.

Accordingly, in the closed condition of the valve 60, fluid that has entered the tubular member 21 via the opening 25 cannot pass through the valve 60. In the open condition of the valve 360 fluid that has passed through the opening 25 is able to pass from the tubular member 21 through the open valve 60 into the housing 61 and exit via the opening 78 when the cap 90 has been removed from the housing 61.

In use, when the valve 60 is in its closed condition, the pressure relief valve 94 can be operated to release gas pressure from inside the tubular member 21. This is done by depressing the button 103 to cause the tube 99 to move such that the wider portion 101 enters the hole 95 and compresses the spring 100 between the end of the wider portion 101 and the ledge 106. The tip 107 is moved out of the opening 109 and through the narrow hole 80 in the apex region 81 of the sealing member 62 into the neck 74 which is in communication with the tubular member 21. Gas is then able to exit the tubular member 21 and enter the tube 99 by passing through the opening 108 in the tip 107. The gas then vents from the tube 99 via the apertures 102. In this way, pressure is released from inside the tubular member 21. When the button 103 is released, the spring 100 biases the tube 99 and button 103 back to their original positions. The tip 107 retracts back into the opening 109 and the narrow hole 80 in the apex region 81 of the sealing member 62 closes. The pressure release valve 94 is thereby returned to its closed condition.

The flange member 22 may contain magnetic or magnetised material so that it is attracted to the implant 20. In use, this will operatively associate the implant 10 and the discharge device 20 and removably retain the discharge device 20 at the site of the stoma S, i.e. so that it is positioned and retained at the site of the stoma S.

Securing/Fastening Belt

The securing belt 120 is shown in FIGS. 8, 9A and 9B and can also be seen in FIGS. 1 and 12. The securing belt 120 has a cover, or case, 121 and a strap 122. The strap 122 is attached to the case 121. The strap 122 may be attached at respective opposed locations of the case 121 by its end regions 123 and 124 passing through slits 125 in the case 121 being stitched to the overlapping portions of the strap 122.

The case 121 has a shroud 126 surrounded by a substantially flat portion 127. The case 121 has an opening 128 therethrough. The opening 128, in use, is able to receive the housing 61 and the projecting portion 37 of the flange member 22 such that they are substantially covered by the shroud 126. The shroud 126 is provided with an external screw thread 129, which is located near the substantially flat portion 127. The shroud 126 is also provided with an opening 130. The handle 71 extends through the opening 130 when the shroud 126 covers the housing 61.

In use, the securing belt 120 may be worn around the waist of a user. The strap 122 is provided with a buckle 131 whereby the length of the strap 122 is adjustable so that the securing belt 120 can be adjusted to the required tightness to suit the user.

Retention Ring

Figure 10A:
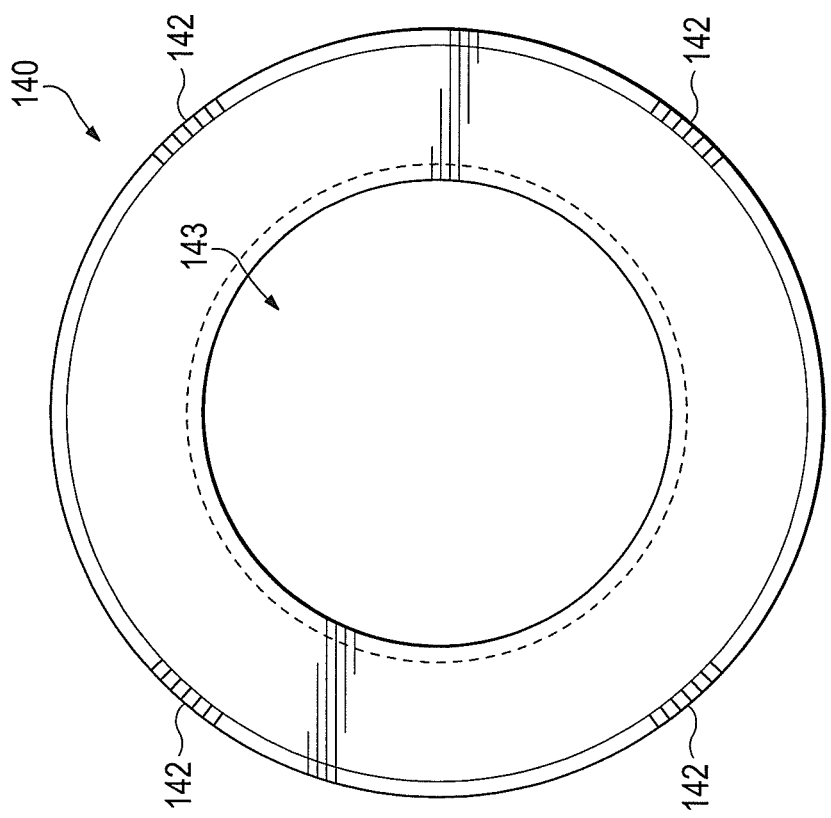
FIG. 10A is an elevation view of the retention ring of the ostomy device shown on FIG. 1.
Figure 10B:
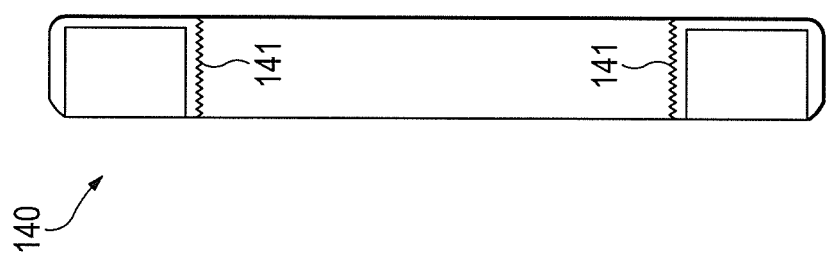
FIG. 10B is a cross sectional side view of the retention ring shown in FIG. 10A.

The retention ring or retention ring 140 is shown in FIGS. 10A and 10B. The retention ring 140 is magnetised so that it creates a magnetic field. This may be done, for example, by embedding or impregnating the retention ring 140 with magnetised material, in a manner similar to that described with reference to the implant 10.

The retention ring 140 is substantially annular, in the form of an annular disc.

The retention ring 140 is provided with a screw thread 141 on its internal circumference. The retention ring 140 is provided with serrated portions 142 on its outer circumference. The retention ring has a central opening 143.

In use, the implant 10 and retention ring 140 are operatively associated by being magnetically attracted to each other as will be further described later herein.

Manner of Use

The manner of operation and use of the ostomy device 1 of the present invention of will now be described.

When a person requires the use of an ostomy device 1 of the present invention, the person undergoes surgery to have an ostomy created in the usual manner. The following description is with particular reference to FIG. 12. The surgery requires that an incision is made in the abdominal wall W of the person. One end 13 or 14 of the implant 10 is inserted through the incision, made in the abdominal wall W, until the entire implant 10 is contained within the abdomen A of the patient. The pins 15 are then inserted into the aligned holes provided in the abutting and overlapped cut-out portions, at the end regions 13 and 14, to connect the end regions 13 and 14 together. The implant 10 is then located around the incision and sutured to the abdominal wall W using the holes 12 in the implant 10. The implant 10 must be sterile since it is sutured inside the body of the patient. The intestine I of the patient, either the large or the small intestine, is cut and an end pulled through the incision and sutured to the skin at the outside of the incision to form a stoma S. In this way, the portion of the intestine I used to form the stoma S passes through the opening 16 of the implant 10.

This completes the part of the installation of the ostomy device 1 that requires surgery.

The use and operation of the discharge device 20 and the securing belt 120, as will now be described, is performed by the person, whenever required.

The tubular member 21 must be inserted into the intestine I via the stoma S. This can be done without the housing 61 connected with the ostomy insertion device 50 which will allow the person to inject air into the bladder 33 via the inlet 41. The air can be injected via a syringe. The bladder 33 can be inflated so that the surface of the bladder 33 is in close contact with the stoma S. This ensures that the stoma S is shielded, reduces the risk of necrosis at the stoma S and seals around the site of the stoma S.

Alternatively, the housing 61 can be connected to the ostomy insertion device 50 after the tubular member 21 has been inserted into the intestine I. The cap 90 may be already connected to the housing 61 when the housing is connected to the ostomy insertion device 50 or it may be connected to the housing 61 after the housing 61 has been connected to the ostomy insertion device.

Figures 11A, 11B:
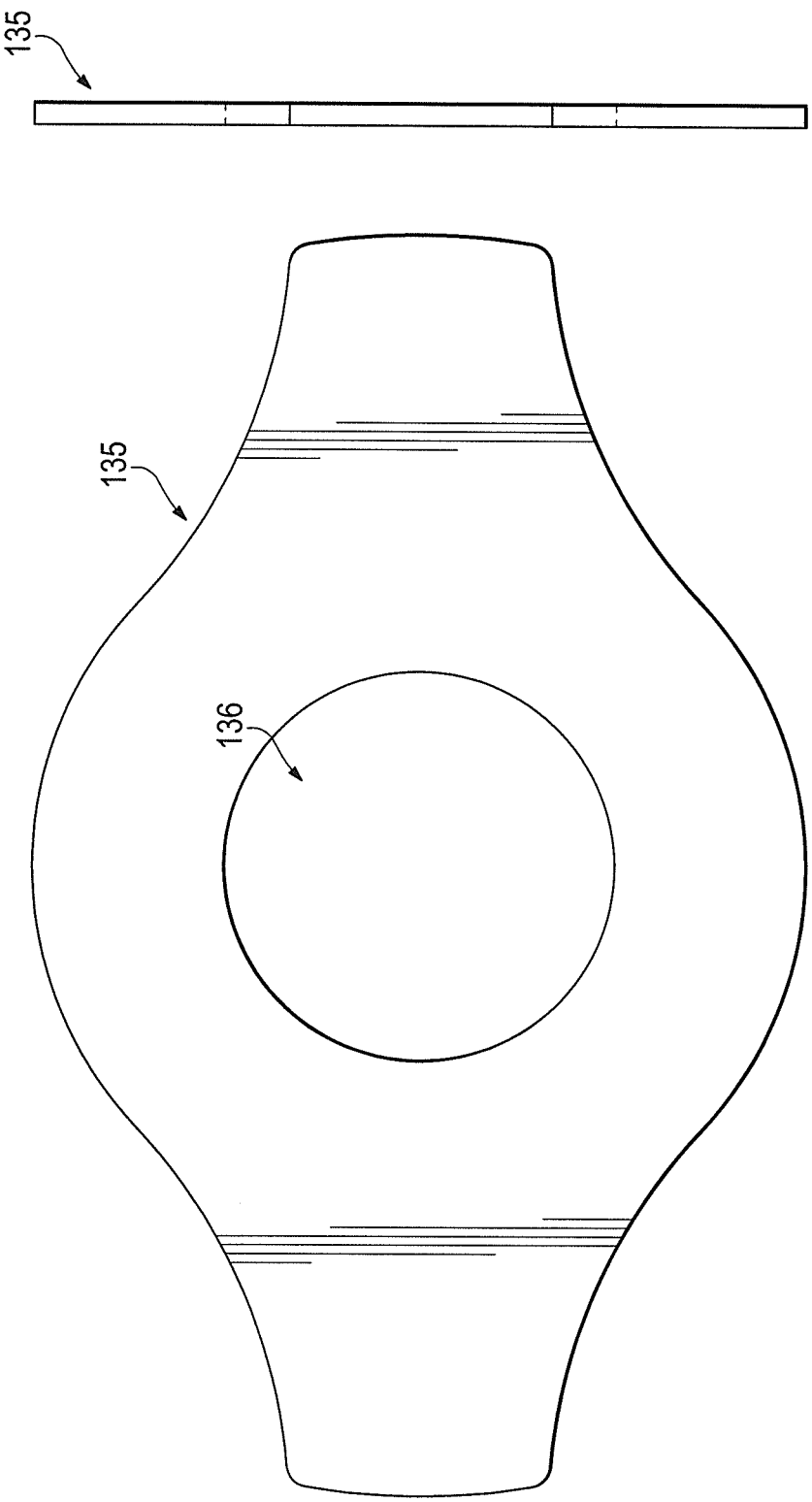
FIG. 11A is a plan view of the gauze pad that may be used with the securing belt.
FIG. 11B is a side view of the gauze pad shown in FIG. 10A.

Prior to insertion of the tubular member 21 into the intestine I, a gauze pad 135 may be placed against the skin of the person around the site of the stoma S. The gauze pad 135 is shown in FIGS. 11A and 11B. The gauze pad 135 has a hole 136 and has substantially the same profile shape as the substantially flat portion 127 of the case 121. The hole 136 in the gauze pad 135 is aligned with the opening 128 of the case 121. The hole 136 accommodates the stoma S. The tubular member 21 is then inserted into the intestine I by guiding the end 26 of the tubular member 21 into the intestine I via the stoma S. In this way the end 25 is the leading end of the tubular member 21. The tubular member 21 is then inserted into the intestine I via the stoma S until the entire tubular member 21 is located in the intestine I and the flange member 22 abuts with the skin of the person adjacent the stoma S. The ribs 27 in the tubular member 21 provide the tubular member with a degree of rigidity such that the tubular member 21 maintains its shape and does not become collapsed as it is inserted though the stoma S into the intestine I. The exterior surface of the tubular member 21 lies adjacent the interior surface of the wall of the intestine I. A continuous lumen is formed by the lumen of the intestine i and the tubular member 21.

If the flange member 22 contains magnetic or magnetised material, it will be attracted to the implant 10, which is itself magnetised. The force with which the implant 10 and the flange member 22 are attracted can be predetermined. For example, if the flange member 22 is to contain magnetic material, the necessary amount of magnetic material can be used to achieve the required force of magnetic attraction between the implant 10 and the flange member 22. If the flange member 22 is to be magnetised, the flange member 22 can be given the necessary magnetic field strength to achieve the required force of magnetic attraction between the implant 10 and the flange member 22

The raised formation of the stoma S is accommodated by the recess 28 and is in contact with the bladder 33.

When the discharge device 20 is in position at the site of the stoma S, the valve 60 is orientated such that the rotational axis 69 of the shaft 68 is in a substantially horizontal position when the abdomen of the person is in an upright position, e.g. when the person is standing or sitting.

The case 121 is placed in position, such that the housing 61 passes through the opening 128 and the substantially flat portion 127 of the case 121 is located adjacent the body of the person, with the gauze pad 135 between the substantially flat portion 127 and the skin of the person. The shroud 126 substantially covers the housing 61 and the projecting portion 37 of the flange member 22 and the substantially flat portion 29 covers the outer portion 29 of the flange member 22. The strap 122 and buckle 131 can be used to adjust the belt 120 around the waist of the person.

The retention ring 140 is attached to the belt 120 by passing the central opening 143 of the retention ring 140 over the shroud 126 and engaging the screw thread 141 on the retention ring 140 with the screw thread 129 on the shroud 126 of the case 121. The serrated portions 142, on the retention ring 140, provide frictional grips for the user to grip the retention ring 140 to screw, and unscrew, the retention ring 140 onto, and from, the case 121. The magnetic attraction between the implant 10 and the retention ring 140 sandwiches the flange member 22 and the case 121 between the implant 10 and the retention ring 140. This procedure locates and retains the discharge device 20 at the site of the stoma S. The case 121 also acts as a spacer between the implant 10 and the retention ring 140. The provision of the screw threads 129 and 141 allows the person to adjust the distance between the implant 10 and the retention ring 140. This allows the attractive force between the implant 10 and the retention ring 140 to be adjusted as desired by the person.

In an alternative mode of use, the securing belt 120 may be omitted and the retention ring 140 passed over the housing 61 until it abuts with the flange member 22. The magnetic attraction between the implant 10 and the retention ring 140 sandwiches the flange member 22 therebetween. This keeps the discharge device 20 in place with the tubular member 21 located in the intestine I.

Over long periods of time, there is a risk that this alternative mode of use may, however, lead to late skin necrosis. This may arise due to the magnetic attraction between the implant 10 and the retention ring 140. A powerful magnetic attraction between the implant 10 and the retention ring 140 may result in a reduction or slowing of blood circulation at the site around the stoma S. This could eventually destroy surrounding cells and result in skin necrosis. The risk of late skin necrosis may, however, be mitigated by reducing the periods during which this alternative mode is used and also by using spacers between the flange member 22 and the retention ring 140.

In normal use, the ostomy device 1 is positioned at the site of the stoma S, as herein before described, and the valve 60 is in its closed condition. Since the valve 60 is in its closed condition, any intestinal waste is retained in the intestine I and in the tubular member 21. When the person requires to empty the intestine I, the person removes the cap 90 from the housing 61 and then turns the handle 71 to move the valve 60 to its open condition over a suitable receptacle, such a toilet pan. The intestinal waste is then discharged from the intestine I and the tubular member 21, through the open valve 60 and out via the opening 78 of the housing 61. The person may then clean the discharge device 20, if required. This is done by removing the retention ring 140 and the belt 120 and then removing the tubular member 21 from the stoma S. The discharge device 20 can then be cleaned with an appropriate cleaning preparation. The person may also inspect the stoma S and attend to any cleaning if required. However, since the intestinal waste does not come into contact with the stoma S when the intestinal waste is discharged, the need to clean the stoma S will occur less frequently than when using an ostomy bag of the prior art. The handle 71 is used to return the valve 60 to its closed condition. The discharge device 20 is then repositioned at its location at the site of the stoma S as previously herein before described.

Intestinal gases may be released as required using the pressure relief valve 94 as previously herein described.

The ostomy insertion device 50 may be replaced periodically, for example, monthly. This will assist in maintaining the hygiene and cleanliness of the stoma S.

Variations

Further Embodiments

As previously hereinbefore described, the discharge device 20 of the ostomy device 1 of the present invention is retained in position, at the site of the stoma S by magnetic attraction. In the embodiments described, this magnetic attraction arises because the implant 10 is magnetised and the retention ring 140 is magnetised.

However, there are various variations of the components of the ostomy device 1 of the present invention that may be magnetised so as to create the necessary magnetic field to provide the magnetic attraction to retain the discharge device 20 at the site of the stoma S and be attracted to the implant 10.

In a first variation, only the implant 10 is magnetised. The retention ring 140 is made of magnetic material, which is attracted to the magnetised implant 10. In this embodiment, the flange member 22 of the discharge device 20 may, or may not, be magnetised or magnetic.

In a second variation, the implant 10 is magnetic, but not magnetised. The retention ring 140 is magnetised to create the magnetic attraction between the retention ring 140 and the implant 10. In this variation, the flange member 22 of the discharge device 20 may, or may not, be magnetised or magnetic.

In a third variation, the implant 10 is magnetised and the flange member 22 of the discharge device 20 is also magnetised. In this variation, the retention ring 140 and the securing belt 120 may either be omitted, or the retention ring 140 may be magnetic or magnetised.

In a fourth variation, the implant 10 is magnetic, though not magnetised. The flange member 22 of the discharge device 20 is magnetised to create the magnetic attraction between the implant 10 and the flange member 22 to thereby retain the discharge device 20 in place. In this variation, the retention ring 140 and the securing belt 120 may be omitted such that the flange member 22 is the means of retention to be operatively associated with the implant 10 and removably locate the discharge device 20 at the site of the stoma S. Alternatively, the retention ring 140 may be magnetic or magnetised, and optionally, the securing belt 120 may be used as well.

Modifications and variations such as would be apparent to a skilled addressee are deemed to be within the scope of the present invention.

The invention claimed is:
1. An ostomy device, comprising:
an implant configured to be located inside a body of a person near a site of a stoma;

a discharge device that is capable of use in an intestine of the person, the discharge device having a tubular member, and at least one of an annular disc and a flange member,
  the tubular member including a first end and a second end with a respective opening at each end, the first end is insertable into the intestine of the person via the stoma such that the tubular member is positionable in the intestine of the person to discharge fluid and materials from inside the intestine through the opening at the first end of the tubular member to the opening at the second end of the tubular member to an exterior of the body of the person, the intestine used to form the stoma, and
  the at least one of the annular disc and the flange member is provided at the second end of the tubular member such that the tubular member extends from the at least one of the annular disc and the flange member on a first side of the at least one of the annular disc and the flange member, and the at least one of the annular disc and the flange member is positioned to bear against the exterior of the body of the person near the site of the stoma when the tubular member is positioned in the intestine of the person,
a retention member structured to be operatively associated with the implant, the implant and the retention member being magnetically attracted such that the discharge device is removably retained at the site of the stoma by magnetic force; and
a user-operable discharge control valve structured to open and close to thereby control the discharge of the fluid and materials to the exterior of the body of the person such that fluid and materials are dischargeable from the tubular member to the exterior of the body of the person when the discharge control valve is in an open position and fluid and materials are not dischargeable from the tubular member to the exterior of the body of the person when the discharge control valve is in a closed position,
  wherein the at least one of the annular disc and the flange member are provided with a recess at the first side of the at least one of the annular disc and the flange member and are positioned adjacent to the second end of the tubular member such that the recess extends around the second end of the tubular member in a circular manner and is aligned over the stoma when the tubular member is positioned in the intestine of the person; and
  wherein an annular inflatable bladder is positioned in the recess adjacent to the second end of the tubular member to closely contact the stoma and to shield the stoma and seal around the site of the stoma at the exterior body of the person when the tubular member is positioned in the intestine of the person; and
  wherein the user-operable discharge control valve is located adjacent to the second end of the tubular member to discharge fluid and materials from the opening at the second end of the tubular member and through the user-operable discharge control valve when the user-operable discharge control valve is in the open position, to exit the ostomy device to the exterior of the body of the person when the tubular member is positioned in the intestine of the person.

2. An ostomy device according to claim 1, wherein the implant is flexible.

3. An ostomy device according to claim 1, wherein the at least one of the annular disc and the flange member has an annular plate portion that surrounds the recess and is positioned to bear against the exterior of the body of the person near the site of the stoma when the tubular member is positioned in the intestine of the person.

4. An ostomy device according to claim 1, wherein the discharge device comprises a first portion and a second portion detachably connected together, the first portion including the tubular member and the second portion including the user-operable discharge control valve.

5. An ostomy device according to claim 1, wherein the user-operable discharge control valve comprises:
  a housing;
  a sealing member mounted in the housing and movable from a first, closed position, in which the user-operable discharge control valve does not allow the fluid and materials to discharge through the user-operable control valve, to a second, open position, in which the user-operable discharge control valve allows the fluid and materials to flow through the discharge device; and
  a handle operable to move the sealing member between the first and second positions to open and close the user-operable discharge control valve,
  wherein the handle is operable to open and close the user-operable discharge control valve to control the discharge of the fluid and materials to the exterior of the body of the person.

6. An ostomy device according to claim 5, wherein the user-operable discharge control valve further comprises a valve seat and the sealing member has a convex surface and a concave surface on respective opposed faces thereof, wherein the convex surface is in contact with the valve seat when the sealing member is in the closed position and the convex surface is positioned adjacent an inner surface of the housing and is spaced apart from the valve seat when the sealing member is in the open position and the convex surface is provided at an upstream side of the sealing member in the direction of fluid flow through the discharge device.

7. An ostomy device according to claim 5, wherein the housing has a neck having a diameter less than the diameter of the portion of the housing that accommodates the sealing member and the valve seat is provided between the neck and the portion of the housing that accommodates the sealing member.

8. An ostomy device according to claim 1, further comprising a pressure relief valve structured to release gas pressure from inside the tubular member at an upstream side of the direction of fluid flow through the user-operable discharge control valve when the user-operable discharge control valve is in the closed position, the pressure relief valve also structured to vent gas from the pressure relief valve.

9. An ostomy device according to claim 5, further comprising a pressure relief valve structured to release gas pressure from inside the tubular member at an upstream side of the direction of fluid flow through the user-operable discharge control valve, when the user-operable discharge control valve is in the closed position, the pressure relief valve also structured to vent the gas from the pressure relief valve, the pressure relief valve having a tube and a closable hole in the sealing member such that a tip of the tube is moveable through the closable hole in the sealing member to allow gas from the upstream side of the sealing member to exit and vent through the tube, and the tube is moveable to retract the tip and close the closable hole to return the pressure relief valve to the closed condition.

10. An ostomy device according to claim 9, wherein the pressure relief valve further comprises a spring to bias the tube such that the tip is retracted in the closed position of the pressure relief valve.

11. An ostomy device according to claim 10, further comprising a removable cap structured to close an end of the housing and accommodate the pressure relief valve.

12. An ostomy device according to claim 4, further comprising a securing member, structured to secure the discharge device at the site of the stoma, the securing member including a case positioned between the retention member and the site of the stoma to cover the second portion of the discharge device.

13. An ostomy device according to claim 12, wherein the retention member is removably mounted to the case.

14. An ostomy device according to claim 1, wherein the retention member includes a ring or annular disc.

15. An ostomy device according to claim 1, wherein the magnetic force between the implant and the retention member is adjustable by a user by adjusting the distance between the implant and the retention member.

16. An ostomy device according to claim 15, further comprising at least one spacer structured to adjust the distance between the implant and the retention member.

17. An ostomy device according to claim 1, wherein the at least one of the annular disc and the flange member has an inlet structured to inject air into the annular inflatable bladder to inflate the annular inflatable bladder.

18. An ostomy device according to claim 1, wherein the retention member includes the at least one of the annular disc and the flange member of the discharge device.

19. An ostomy device according to claim 1, wherein the user-operable discharge control valve is operable without engaging the tubular member.

20. An ostomy device according to claim 1, wherein the user-operable discharge control valve is operable independently of the operative association of the retention member and the implant.

21. A fluid flow control valve for a medical device comprising:
a housing;
a sealing member mounted in the housing and movable from a first, closed position, in which the fluid flow control valve is in a closed position, to a second, open position, in which the fluid flow control valve is in an open position to allow fluid and materials to flow through the fluid flow control valve;
a handle operable to move the sealing member between the first and second positions to open and close the fluid flow control valve; and
a pressure relief valve provided to release gas pressure when the sealing member is in the closed position, the gas pressure relief at an upstream side of the sealing member in the direction of the fluid and materials flow through the fluid flow control valve, the pressure relief valve also provided to vent the gas from the pressure relief valve,
wherein the pressure relief valve has a tube and the sealing member has a closable hole, such that a tip of the tube is moveable through the closable hole in the sealing member to allow gas from the upstream side of the sealing member to exit and vent through the tube, and the tube is moveable to retract the tip and close the closable hole to return the pressure relief valve to the closed condition, and
wherein the fluid flow control valve is arranged in the medical device and the handle is operable to move the sealing member to the open and closed positions to control the flow of fluid and materials through the fluid flow control valve when the medical device is in use in the body of a person.

22. A fluid flow control valve according to claim 21, further comprising a valve seat, the sealing member has a convex surface and a concave surface on respective opposed faces thereof, wherein the convex surface is in contact with the valve seat when the fluid flow control valve is in the closed position and the convex surface is positioned adjacent an inner surface of the housing and is spaced apart from the valve seat when the fluid flow control valve is in the open position.

23. A fluid flow control valve according to claim 22, wherein the convex surface is provided at an upstream side of the sealing member in the direction of fluid flow through the fluid flow control valve.

24. A fluid flow control valve according to claim 21, wherein the housing has a neck having a diameter less than the diameter of the portion of the housing that accommodates the sealing member and the valve seat is provided between the neck and the portion of the housing that accommodates the sealing member.

25. A fluid flow control valve according to claim 21, wherein the pressure relief valve further comprises a spring to bias the tube such that the tip is retracted in the closed position of the pressure relief valve.

26. A fluid flow control valve according to claim 21, further comprising a removable cap structured to close an end of the housing and accommodate the pressure relief valve.

27. An ostomy insertion device, comprising:
a tubular member, which is capable of use in the body of a person, having a first end and a second end with a respective opening at each end, the first end configured to be inserted into the body of a person to position the tubular member in the body of the person to discharge fluid and materials from inside the body of the person from the opening at the first end of the tubular member to the opening at the second end of the tubular member to an exterior of the body of a person,
at least one of an annular disc and a flange member positioned at a second end of the tubular member such that the tubular member extends from the at least one of the annular disc and the flange member on a first side of the at least one of the annular disc and the flange member, and the at least one of the annular disc and the flange member is positioned to bear against the exterior of the body of the person when the tubular member is positioned in the body of the person;
the at least one of the annular disc and the flange member having a recess and an annular plate portion positioned around the recess, the recess located at the first side of the at least one of the annular disc and the flange member and adjacent to the second end of the tubular member such that the recess extends around the second end of the tubular member in a circular manner, and
the recess having an annular inflatable bladder positioned therein, adjacent to the second end of the tubular member,
wherein the recess is aligned over a stoma of the person when the tubular member is positioned in the body of the person, and the annular plate portion bears against the body of the person near a site of the stoma, and the annular inflatable bladder being inflatable such that inflating the bladder causes the annular inflatable bladder to come in close contact with the stoma to shield the stoma and create a seal around the site of the stoma at the exterior of the body of the person when the tubular member is positioned in the body of the person.

28. An ostomy insertion device according to claim 27, wherein the at least one of the annular disc and the flange member includes an inlet structured to inject air into the annular inflatable bladder to inflate the annular inflatable bladder.

* * * * *